(12) United States Patent
Hirano et al.

(10) Patent No.: US 7,422,907 B2
(45) Date of Patent: Sep. 9, 2008

(54) PROCESS FOR MEASURING MERCURY CONCENTRATION WITHIN HYDROCARBONS

(75) Inventors: Hitomi Hirano, Chiba (JP); Shinichi Okada, Chiba (JP); Naohide Tsuzuki, Nagareyama (JP); Yoshio Yasuda, Funabashi (JP)

(73) Assignee: Sekiyushigen Kaihstsu Kabushiki Kaisha, Tokyo (JP)

(*) Notice: Subject to any disclaimer, the term of this patent is extended or adjusted under 35 U.S.C. 154(b) by 11 days.

(21) Appl. No.: 11/050,914

(22) Filed: Feb. 4, 2005

(65) Prior Publication Data

US 2005/0186678 A1 Aug. 25, 2005

(30) Foreign Application Priority Data

Feb. 19, 2004 (JP) ............................. 2004-042892

(51) Int. Cl.
- *G01N 31/12* (2006.01)
- *G01N 21/00* (2006.01)
- *G01N 33/00* (2006.01)
- *G01R 13/30* (2006.01)

(52) U.S. Cl. .................... 436/81; 436/84; 436/139; 436/140; 436/141; 436/142; 436/143; 436/144; 436/164; 422/82.05; 73/1.56

(58) Field of Classification Search ............... 436/84, 436/164, 81, 139–144; 422/82.05; 73/1.56
See application file for complete search history.

(56) References Cited

U.S. PATENT DOCUMENTS

| | | | |
|---|---|---|---|
| 3,884,639 A | | 5/1975 | Sugiyama |
| 4,023,929 A | | 5/1977 | Becker et al. |
| 5,660,795 A | * | 8/1997 | Schaedlich et al. ............ 422/88 |
| 6,268,543 B1 | * | 7/2001 | Sakai et al. .................. 585/836 |
| 6,829,918 B2 | * | 12/2004 | Tanida et al. ................ 73/23.39 |
| 2003/0180187 A1 | * | 9/2003 | Noda et al. .................... 422/92 |

FOREIGN PATENT DOCUMENTS

| | | | |
|---|---|---|---|
| JP | S61-155765 | | 3/1985 |
| JP | 2001-221787 | * | 8/2001 .................. 436/84 |

(Continued)

OTHER PUBLICATIONS

Esterling, D.F and Hovanitz, E.S., Comparison of Adsorbed Mercury Screening Method With Cold-Vapor Atomic Absorption Spectrophotometry for Determination of Mercury In Soil, National Aeronautics and Space Administration, Mar. 2000.*

(Continued)

*Primary Examiner*—Jill Warden
*Assistant Examiner*—Keri A Moss
(74) *Attorney, Agent, or Firm*—Kolisch Hartwell, P.C.

(57) ABSTRACT

A process for measuring the mercury concentration within a hydrocarbon is provided that enables the mercury concentration to be measured simply and quickly, and with good reliability and good reproducibility. A process for measuring the mercury concentration within a hydrocarbon includes the steps of placing and weighing the hydrocarbon in a sample boat 12 containing an adsorbent that contains a metal capable of forming an amalgam with mercury, and heating the hydrocarbon inside the sample boat 12 in a combustion furnace 13, together with the adsorbent, and measuring the quantity of mercury within the thus generated gas.

4 Claims, 1 Drawing Sheet

FOREIGN PATENT DOCUMENTS

JP        2003-240687        8/2003

OTHER PUBLICATIONS

Wilhelm, S.M and Bloom, N., Mercury in petroleum, Fuel Processing Technology 63 (2000) 1-27.*

European Search Report for European Application No. EP 05290261 dated Jul. 14, 2005.

Office Action drafted on Mar. 16, 2004, issued on the counterpart Japanese Patent Application No. 2004-42892 and its English translation.

* cited by examiner

PROCESS FOR MEASURING MERCURY CONCENTRATION WITHIN HYDROCARBONS

BACKGROUND OF THE INVENTION

1. Field of the Invention

The present invention relates to a process for measuring the mercury concentration within hydrocarbons such as crude oil.

2. Description of Related Art

Hydrocarbons such as crude oil can contain organic mercury, metallic mercury and ionic mercury. Because this mercury can have a deleterious impact on the environment, the catalysts used in the production of all manner of petrochemical products, and the metals used in the construction of associated production equipment, accurately ascertaining the mercury concentration within crude oil is very important. Conventionally, a sample is extracted from the crude oil and heated to generate a gas that contains the mercury, and the level of mercury in the gas is then measured (for example, Japanese Patent application, first Publication No. 2001-221787).

Measurement of the mercury concentration within a hydrocarbon sample using the heating and vaporization method is conducted in the manner described below.

First, in a sample boat containing activated alumina, the hydrocarbon sample is placed and weighed, and additional activated alumina is then placed on top of the sample. Sodium carbonate and calcium hydroxide, which can remove gases interfering with the mercury measurement, are then added. The sample boat is then placed in the combustion furnace of a combustion-type mercury measurement device, and with air flowing through the furnace, the sample is heated, thus generating a gas containing the mercury in vapor form. This gas containing the mercury vapor is then passed through a column packed with gold carrying diatomaceous earth, together with the air flowing through the furnace. As the gas containing the mercury vapor passes through the column, the mercury forms an amalgam with the gold of the gold carrying diatomaceous earth, and is thus trapped by the gold carrying diatomaceous earth. Following trapping of the mercury, the gold carrying diatomaceous earth is heated under a stream of air, generating a gas containing the mercury vapor, and this gas is then fed into a cold atomic absorption detector to measure the quantity of mercury within the gas.

However, when repeated measurements of the mercury concentration are conducted on the same hydrocarbon sample using this method, the value for the mercury concentration changes with each measurement, and the variation in the mercury concentration can be as much as ± several tens percent. Furthermore, when the results are compared with the mercury concentration measured using a different method, which although being both time and labor intensive, is comparatively more accurate, the results from the more convenient method described above are only about ¼ of the value of the more accurate result, meaning the measured mercury concentration values are not particularly reliable.

Patent Reference 1

Japanese Unexamined Patent Application, First Publication No. 2001-221787

(as described in the related art)

SUMMARY OF THE INVENTION

An object of the present invention is to provide a process for measuring the mercury concentration within a hydrocarbon that enables the mercury concentration to be measured simply and quickly, and with good reliability and good reproducibility.

As a result of intensive investigation aimed at achieving the above object, the inventors of the present invention discovered that in the conventional hydrocarbon heating and vaporization method, the majority of the metallic mercury from the sample vaporizes in the period between weighing the sample and transporting the sample to the combustion furnace, and they were consequently able to complete the present invention.

In other words, a process for measuring the mercury concentration within a hydrocarbon according to the present invention comprises the steps of placing and weighing the hydrocarbon in a sample boat containing an adsorbent that comprises a metal capable of forming an amalgam with mercury, and heating the hydrocarbon inside the sample boat, together with the adsorbent, and measuring the weight of mercury within the thus generated gas.

The adsorbent is preferably gold carrying diatomaceous earth.

This process for measuring the mercury concentration within a hydrocarbon according to the present invention enables the mercury concentration within the hydrocarbon to be measured simply and quickly, with good reliability and good reproducibility.

Furthermore, if gold carrying diatomaceous earth is used as the adsorbent, then the mercury concentration can be measured with even greater reliability and reproducibility.

DETAILED DESCRIPTION OF THE INVENTION

Figure 1:
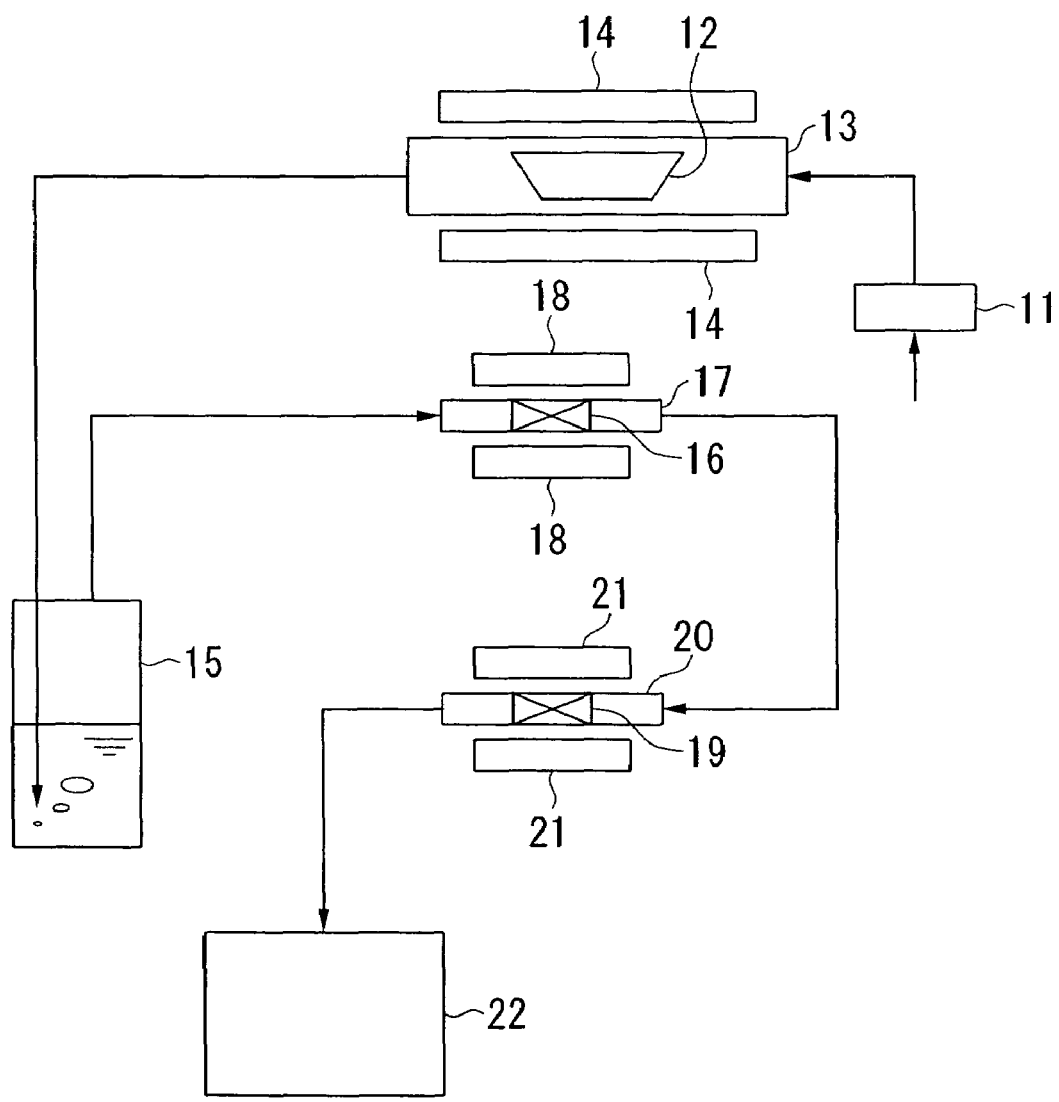
FIG. 1 is a schematic illustration of a sample combustion-type mercury measurement device used for measuring the mercury concentration.

As follows is a more detailed description of the present invention.

A process for measuring the mercury concentration within a hydrocarbon according to the present invention comprises a step for placing and weighing the hydrocarbon in a sample boat containing an adsorbent (hereafter referred to as the "weighing step"), and a step for heating the hydrocarbon inside the sample boat, together with the adsorbent, and measuring the weight of mercury within the thus generated gas (hereafter referred to as the "measurement step").

(Weighing Step)

First, the adsorbent is placed in the empty sample boat. The hydrocarbon sample is then placed in the sample boat containing the adsorbent, and the weight of the hydrocarbon is measured.

The adsorbent comprises a metal capable of forming an amalgam with mercury, and suitable adsorbents include metals such as gold, silver, tin, aluminum, and copper, as well as porous materials in which these types of metals are supported within the pores of the porous material. Of these adsorbents, porous material-supported metal adsorbents are preferred as they provide a superior contact surface area between the sample and the adsorbent, and display a large mercury adsorbing effect, even with small quantities of metal.

Gold is the preferred metal for use within the adsorbent as it readily forms an amalgam with mercury, and is chemically stable meaning it can be reused repeatedly. Furthermore, the porous material carrier is preferably capable of withstanding high temperatures, while being unreactive with respect to the sample and the supported metal, and suitable examples include diatomaceous earth and zeolite. Of these, diatomaceous earth is particularly preferred. Accordingly, the adsorbent in the present invention is most preferably gold carrying diatomaceous earth.

There are no particular restrictions on the weight of the adsorbent, although in order to efficiently suppress the vaporization of metallic mercury, the weight of adsorbent is preferably sufficient to provide from 100 to 1,000 parts by weight of the metal capable of forming an amalgam with mercury per 100 parts by weight of the sample.

The sample boat must be capable of holding the sample and the adsorbent, capable of withstanding high temperatures, and be unreactive with respect to the sample and the adsorbent, and the types of sample boats used in conventional mercury concentration measurements, such as ceramic sample boats, are ideal.

(Measurement Step)

FIG. 1 is a schematic illustration showing one example of a combustion-type mercury measurement device used for measuring the mercury concentration within a hydrocarbon sample. This combustion-type mercury measurement device comprises, as its main components, a filter 11 for removing mercury from the air, a combustion furnace 13, inside which is placed the sample boat 12, a heater 14 that is integrated with the combustion furnace 13, a washing tank 15 for washing the gas generated within the combustion furnace 13, a first column 17 packed with an adsorbent 16 for trapping the mercury, a heater 18 that is integrated with the first column 17, a second column 20 packed with an adsorbent 19 for trapping the mercury, a heater 21 that is integrated with the second column 20, a cold atomic absorption detector 22 for measuring the quantity of mercury vapor within a vaporized gas from the adsorbent 16 and the adsorbent 19, and a suction pump (not shown in the figure) for generating an air flow from the filter 11 through to the cold atomic absorption detector 22.

The filter 11 is packed with an adsorbent capable of trapping mercury. The adsorbents packed inside the filter 11 and each of the columns 17 and 20 may be the same as the adsorbent placed in the sample boat 12. The adsorbent may also contain the types of additives typically used in conventional methods.

The washing liquid provided within the washing tank 15 can use, for example, a neutral phosphate pH standard solution.

Measurement of the mercury concentration within a hydrocarbon using this combustion-type mercury measurement device is conducted in the manner described below.

First, the sample boat 12 containing the sample and adsorbent is placed inside the combustion furnace 13. Then, with mercury-free air that has passed through the filter 11 flowing through the combustion furnace 13, the sample and the adsorbent are heated using the heater 14, thereby decomposing the sample and generating a gas that contains mercury vapor. This gas containing the mercury vapor is carried into the washing tank 15 by the air flow, and following washing, passes though the first column 17 and the second column 20. As the gas containing the mercury vapor passes through the first column 17 and the second column 20, the mercury forms an amalgam with the metal supported on the adsorbent, and is thus trapped within the adsorbents 16 and 19. Once the sample within the sample boat 12 has completely decomposed and any mercury has been trapped within the adsorbents 16 and 19, the air flow is continued, and the heaters 18 and 21 are used to heat the adsorbents 16 and 19 respectively, thus re-vaporizing the trapped mercury and feeding a gas containing mercury vapor into the cold atomic absorption detector 22, where the weight of mercury within the gas is then measured.

The temperature inside the combustion furnace 13 during heating of the sample boat 12 is typically within a range from 350 to 970° C.

Furthermore, the temperature inside the columns during heating of the adsorbents 16 and 19 is typically within a range from 150 to 600° C.

The flow rate of the air flowing through the device is typically within a range from 0.3 to 0.8 L/min.

In the process for measuring the mercury concentration within a hydrocarbon according to the present invention described above, because the sample and the adsorbent coexist during both the weighing of the sample, and the period between the weighing of the sample and the transporting of the sample into the combustion furnace 13, the metallic mercury within the sample forms an amalgam with the metal contained within the adsorbent, and is retained within the sample boat 12 and prevented from vaporizing. As a result, those problems associated with the fact that, in the conventional technology, the majority of the metallic mercury from the sample vaporizes in the period between weighing the sample and transporting the sample to the combustion furnace 13, namely, a significant variation in the observed mercury concentration on each measurement, and a large deviation of the measured value from the true value, can be suppressed to a minimum.

EXAMPLES

As follows is a description of an example and a comparative example.

Example 1

An SP-3D device manufactured by Nippon Instruments Corporation, with a structure similar to that shown in FIG. 1, was used as the combustion-type mercury measurement device. The filter 11, the first column 17, and the second column 20 were each packed with 0.5 g of gold carrying diatomaceous earth (designed for mercury collecting tubes, manufactured by Nippon Instruments Corporation). 10 ml of a mixed solution of a neutral phosphate pH standard solution and distilled water was used as the washing liquid.

First, 0.5 g of the gold carrying diatomaceous earth (designed for mercury collecting tubes, manufactured by Nippon Instruments Corporation) was placed in the empty sample boat 12. Subsequently, 0.1 ml of a crude oil sample was placed in the sample boat containing the gold carrying diatomaceous earth, and the weight of the crude oil was measured accurately.

The sample boat 12 containing the crude oil and the gold carrying diatomaceous earth was then placed inside the combustion furnace 13, and with mercury-air free that had passed through the filter 11 flowing through the device at a flow rate of 0.5 L/min, the sample boat 12 was subjected to a two-stage heating process, at 350° C. for 4 minutes, and then at 700° C. for a further 6 minutes.

Then, with mercury-free air that had passed through the filter 11 still flowing through the device at a flow rate of 0.5 L/min, the gold carrying diatomaceous earth within each of the columns was heated at 600° C. for 1.5 minutes, thus vaporizing the mercury that had been trapped by the gold carrying diatomaceous earth, and feeding a gas containing the mercury vapor into the cold atomic absorption detector 22, where the weight of mercury within the gas was measured.

The measured weight of mercury was then divided by the weight of the crude oil to determine the mercury concentration within the crude oil.

Using the same crude oil, the above measurement was repeated a total of 6 times, and the average mercury concentration, the standard deviation, and the coefficient of variation were calculated. The results are shown in Table 1.

Furthermore, another sample of the same crude oil was weighed, and then heated with an aqueous solution containing dissolved sodium sulfide and sodium polysulfide, thereby causing all the mercury within the crude oil to migrate into the aqueous phase (an aqueous phase extraction method). The weight of the mercury within the aqueous phase was then measured, and when the mercury concentration within the crude oil was calculated, the result was 2574 ppb, which was substantially the same result as that observed in the above example.

Comparative Example 1

With the exception of replacing the gold carrying diatomaceous earth that was used as the adsorbent in the sample boat 12 with activated alumina (Type B, manufactured by Nippon Instruments Corporation), the mercury concentration was measured in the same manner as the example 1. The results are showed in Table 1.

Furthermore, when the aforementioned aqueous phase extraction method was used to measure the mercury concentration within a sample of the same crude oil, the result was 2295 ppb, indicating that the measured values from this comparative example 1 were markedly lower than the true mercury concentration.

TABLE 1

|  |  | Example 1 | Comparative example 1 |
|---|---|---|---|
| Measurement iteration | 1 | 2357 ppb | 419 ppb |
|  | 2 | 2566 ppb | 559 ppb |
|  | 3 | 2184 ppb | 657 ppb |
|  | 4 | 2548 ppb | 675 ppb |
|  | 5 | 2664 ppb | 403 ppb |
|  | 6 | 2483 ppb | 699 ppb |
| Average value |  | 2467 ppb | 569 ppb |
| Standard deviation |  | 172 | 131 |
| Coefficient of variation |  | 7% | 23% |
| Aqueous phase extraction method |  | 2574 ppb | 2295 ppb |

According to a process for measuring the mercury concentration within a hydrocarbon of the present invention, measurements can be performed with good reliability and good reproducibility. As a result, the mercury concentration of the crude oil can be determined accurately, and where necessary, the crude oil can then be subjected to suitable mercury removal treatment prior to its use as a raw material for the production of petrochemical products.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the forgoing description, and is only limited by the scope of the appended claims.

What is claimed is:

1. A process for measuring mercury concentration within a hydrocarbon, comprising the steps of:
    weighing a sample boat containing a first adsorbent that comprises a metal capable of forming an amalgam with mercury,
    placing said hydrocarbon in said sample boat containing said first adsorbent,
    weighing said sample boat containing said first adsorbent and said hydrocarbon to determine a weight of said hydrocarbon,
    subsequently transporting said sample boat containing said hydrocarbon and said first adsorbent inside a combustion furnace in a state in which the sample and the first adsorbent coexist during the period between the weighing of the sample and the transporting of the sample into the combustion furnace,
    heating said hydrocarbon inside said sample boat, together with said adsorbent at a temperature sufficient to decompose said sample and generate a gas that contains mercury vapor,
    trapping the generated mercury vapor within a second adsorbent,
    re-vaporizing the trapped mercury and feeding a gas containing the re-vaporized mercury vapor into a cold atomic absorption detector,
    measuring the weight of mercury within said gas using the cold atomic absorption detector, and
    determining the mercury concentration in the hydrocarbon by dividing the weight of mercury by the weight of the hydrocarbon.

2. The process for measuring mercury concentration within a hydrocarbon according to claim 1, wherein said first adsorbent comprises a metal selected from the group of metals capable of forming an amalgam with mercury and a porous material for supporting the metal.

3. The process for measuring mercury concentration within a hydrocarbon according to claim 1, wherein said first adsorbent is gold carrying diatomaceous earth.

4. The process for measuring mercury concentration within a hydrocarbon according to claim 1, wherein said hydrocarbon comprises crude oil.

* * * * *